(12) United States Patent
Curtis et al.

(10) Patent No.: US 6,588,142 B2
(45) Date of Patent: *Jul. 8, 2003

(54) METHOD OF PROTECTING PLANTS FROM COLD INJURY

(75) Inventors: Virginia Lee Curtis, Clayton, NC (US); Jack E. Bailey, Wendell, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/016,002

(22) Filed: Nov. 2, 2001

(65) Prior Publication Data

US 2002/0124462 A1 Sep. 12, 2002

Related U.S. Application Data

(63) Continuation of application No. 09/528,770, filed on Mar. 17, 2000.

(51) Int. Cl.[7] ............................................... A01G 13/00
(52) U.S. Cl. .................. 47/2; 106/13; 252/70
(58) Field of Search .................. 47/58.1, 2; 106/13; 252/70

(56) References Cited

U.S. PATENT DOCUMENTS

| | | | | |
|---|---|---|---|---|
| 4,207,091 A | * | 6/1980 | Fischer | 71/113 |
| 4,331,670 A | * | 5/1982 | Nishiyama et al. | 424/263 |
| 4,432,160 A | * | 2/1984 | Lindow | 47/2 |
| 4,834,899 A | * | 5/1989 | Klevecz | 252/70 |
| 5,133,891 A | * | 7/1992 | Barr et al. | 252/70 |
| 5,276,006 A | | 1/1994 | Shin et al. | 504/140 |
| 5,360,806 A | * | 11/1994 | Toki et al. | 514/318 |
| 5,763,475 A | | 6/1998 | Sato et al. | |
| 5,863,932 A | | 1/1999 | Matsunaga | |
| 5,869,427 A | | 2/1999 | Yoshikawa et al. | |
| 5,919,446 A | * | 7/1999 | Pusey | 424/93.4 |

FOREIGN PATENT DOCUMENTS

JP 01070407 A * 9/1987 .......... A01N/63/00

OTHER PUBLICATIONS

BlightBan A506, MSDS and Label, 4 pages.*
D.E. Legard and C.K. Chandler, Evaluation of Fungicides to Control Botytis and Phomopsis Fruit rot of Strawberry, 1996, University of Florida, 2 pages.*
Pat. M. Phipps, Sclerotinia Attacks Early, Peanut News, Fall 2000, Virginia Tech, pp. 1 and 2.*
T. Hsiang and S. Cook, Chemical Trials for Dollar Spot Disease Control, Summer 1992, University of Guelph, 4 pages.*
Ritichie, D.F. and W. pollan, 1996, Fluazinam 500F for Control of Bacterial Spot of Peach, 1995, Fungicide and Nematicide Tests 51:54.*
Merck Index, 12th Ed., p. 697 (1996).

* cited by examiner

Primary Examiner—Peter M Poon
Assistant Examiner—Andrea M. Valenti
(74) Attorney, Agent, or Firm—Myers Bigel Sibley & Sajovec

(57) ABSTRACT

A method of reducing cold injury or damage to plants such as peanut, citrus trees, peaches, strawberries and other plants susceptible to cold injury such as frost or freezing comprises applying a pyridylaniline active agent such as fluazinam to the plant in an amount effective to reduce cold injury to the plant.

20 Claims, No Drawings

METHOD OF PROTECTING PLANTS FROM COLD INJURY

RELATED APPLICATIONS

This is a continuation of U.S. patent application Ser. No. 09/528,770 filed Mar. 17, 2000, allowed, the disclosure of which is incorporated herein by reference in its entirety.

FIELD OF THE INVENTION

The present invention concerns methods of protecting plants such as citrus trees, peanuts, peaches and strawberries from cold injury, such as damage by frost or freezing.

BACKGROUND OF THE INVENTION

Frost, freeze and other cold damage to plants is a serious agricultural problem. Plants that flower early in the growing season are susceptible to late winter or early spring frost, and plants that are harvested late in the growing season are susceptible to late fall or early winter frost. It has been estimated that approximately 1.5 billion dollars worth of agricultural products are annually lost to freezing temperatures in the United States alone (see U.S. Pat. No. 5,276,006). Among other things, frost injury causes significant damage to citrus, strawberry, peanut and peach crops. Accordingly, there is a need for new ways to combat frost injury to plants.

A variety of approaches to protecting plants from frost and freezing have been suggested. For example, U.S. Pat. No. 5,276,006 to Shin et al. (assigned to Great Lakes Chemical Corp.) describes an aqueous plant cryoprotectant containing a tetrahydrofurfuryl alcohol or tetrahydrofurfuryl amine. U.S. Pat. No. 4,207,091 to Fischer (assigned to Ciba-Geigy Corp.), describes a method of combating frost damage in plants by treating the plants prior to frost with certain hydroxamic acid derivatives. U.S. Pat. No. 4,432,160 to Lindow (assigned to the University of California) suggests inhibiting frost damage by treating plants with antagonistic ice nucleation deficient bacteria to inhibit colonization of the plant by ice nucleation capable bacteria. U.S. Pat. No. 5,133,891 to Barr et al. (assigned to Rhone Poulenc AG Co.), describes a method for combating frost damage by applying aluminum tris-[O-ethyl phosphonate], or fosetyl-Al, apparently to kill ice nucleating bacteria. Nevertheless, there remains a need for new ways to treat plants to reduce damage from frost and freezing.

SUMMARY OF THE INVENTION

The present invention provides a method of reducing cold injury or damage to a plant, including individual plants and plants existing as a crop of like plants. The method comprises applying a pyridylaniline active agent to the plant in an amount effective to reduce cold injury to the plant. A particularly preferred active agent is fluazinam. The methods may be carried out to reduce any type of cold injury, including frost injury and freezing injury.

The present invention is explained in greater detail below. This explanation is not intended to be an exhaustive catalog of all the different embodiments and manners in which the present invention may be carried out, but is intended to be illustrative of particular embodiments of the invention. Numerous variations will be apparent to those skilled in the art.

DETAILED DESCRIPTION OF THE PREFERRED EMBODIMENTS

The present invention may be used to protect any type of plant from frost or freeze injury, including trees, shrubs, herbaceous plants, etc. Plants treated by the invention are typically frost or cold sensitive plants, in that they are susceptible to frost, freezing or cold damage or injury in economically or aesthetically significant amounts. Specific plants that may be protected by the method of the invention include, but not limited to, peanuts, peaches, strawberries, citrus trees (lemon, lime, orange, etc.), cherries, apples, etc, as well as vegetable crops (e.g., beans, peas), as well as ornamental plants. The term "plant" as used herein includes the complete plant or a portion thereof, such as a flowers, fruits, leaves, stems vegetables, roots, tubers, etc.

"Alkyl" as used herein refers to an alkyl group, which may be linear or branched, and saturated or unsaturated. Alkyl groups, as used herein, are preferably saturated.

"Lower alkyl" as used herein refers to an alkyl group which contains 1 to 4 carbon atoms.

"Alkoxy" as used herein refers to a group —O—R, wherein R is alkyl.

"Lower alkoxy" as used herein refers to an alkoxy group which contains 1 to 4 carbon atoms.

"Halogen" as used herein refers to any halogen group, such as fluoro, chloro, bromo, or iodo, preferably chloro.

"Cold injury" means any type of injury to a plant or plant part caused by a decrease in temperature that results in an economic or aesthetic damage to that plant. Such injury may be by frost injury, freezing injury, or a decrease in temperature below that tolerated by the plant even if the temperature does not decrease below freezing (32° F.; 0° C.) (e.g., as seen in orchids).

"Frost injury" as used herein refers to any type of damage to a plant or plant part that results from the deposition of frost on the surface thereof, whether that frost is natural frost or frozen water or water vapor deposited upon the plant or plant part by artificial means. Such damage includes, but is not limited to, reduced yield, blemishes or other damage that decreases the quality or value of the plant or plant part without reducing yield, etc.

"Freeze injury" as used herein refers to any type of damage to a plant or plant part that results from the formation of ice crystals in at least some cells of that plant, whether or not the ice crystals are formed by natural means due to decreased ambient temperature or artificial cooling or refrigeration. Again, such damage includes, but is not limited to, reduced yield, blemishes or other damage that decrease the quality or value of the plant or plant part without reducing yield, etc.

Active compounds that may be used to carry out the present invention are, in general, pyridylanilines of Formula I:

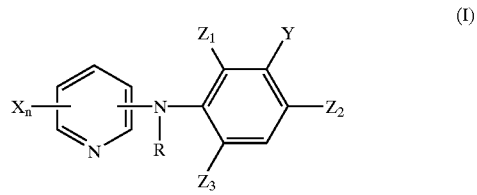

wherein X is a trifluoromethyl group, a halogen atom, a lower alkyl group or a lower alkoxy group; n is an integer of 0 to 4; R is a hydrogen atom or an acetyl group; Y is a hydrogen atom, a halogen atom, a lower alkoxy group, a lower alkylthio group, a hydroxy group, an azido group or a phenoxy group of which the phenyl ring may be substituted by a hydroxy group; and $Z_1$, $Z_2$, and $Z_3$ are independently a trifluoromethyl group or a nitro group; provided that at least one of X is a trifluoromethyl group or a lower alkyl group when n is an integer of 3 or 4.

Preferred compounds of Formula I are those wherein X is a trifluoromethyl group, a halogen atom, a lower alkyl group or a lower alkoxy group; n is an integer of 1 to 4; R is a hydrogen atom or an acetyl group; Y is a hydrogen atom, a halogen atom, a lower alkoxy group, a lower alkylthio group or a hydroxy group; $Z_1$, $Z_2$, and $Z_3$ are a trifluoromethyl group or a nitro group, with the proviso that at least one X is trifluoromethyl and with the proviso that when the X substitution pattern is 3-chloro-5-trifluoromethyl, Y in addition optionally is azido or 2, 3, or 4-hydroxyphenoxy.

Compounds of Formula I are known, and can be made as described in U.S. Pat. No. 4,331,670 to Nishiyama et al. It is specifically intended that all United States patent references cited herein be incorporated herein by reference.

A particularly preferred active compound for carrying out the present invention is fluazinam (or 3-chloro-N-[3-chloro-2,6-dinitro-4-trifluoromethyl)phenyl]-5-trifluoromethyl-2-pyridinamine) (See Merck Index No. 4153 (12th Ed. 1996)), which has the structure of Formula II:

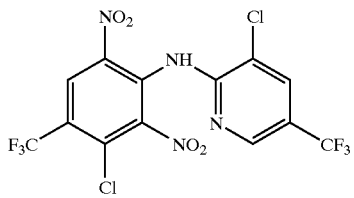

Compounds of Formula II may be made in the same manner as compounds of Formula I above.

Active compounds used herein may be formulated together with agricultural adjuvants and/or carriers into various forms such as dusts, granules, water dispersible granules, wettable powders, emulsifiable concentrations, suspension concentrates, soluble concentrates, water soluble powders, flowables, aerosols or pastes, ultra low-volume formulations, etc. When such formulations are to be actually used, they may be used as is or after being diluted with suitable diluents or carriers such as water.

Such formulations may be composed of 0.01 or 0.1 to 90 or 99 parts by weight of active ingredient, 0.0 or 0.1 to 99.9 parts by weight of agricultural adjuvants, and 0.0 or 0.1 to 99.9 parts by weight of agricultural carrier.

Suitable adjuvants include, but are not limited to, emulsifiers, suspending agents, dispersants, extenders, penetrating agents, wetting agents, thickeners or stabilizers, stickers, combinations of the foregoing, etc. They may be combined with the active agents as the case requires.

The carriers that may be used to carry out the present invention may be classified into solid carriers and liquid carriers. Solid carriers include, but are not limited to, powders of animal and plant origin such as starch, activated carbon, soybean flour, wheat flour, wood powder, fish powder or powdered milk; or mineral powders such as talc, kaolin, bentonite, calcium carbonate, zeolite, diatomaceous earth, white carbon, clay, alumina; combinations of the foregoing; etc. Liquid carriers include, but are not limited to, water, alcohols such as isopropyl alcohol or ethylene glycol; ketones such as cyclohexanone or methyl ethyl ketone; ethers such as dioxane or tetrahydrofuran; aliphatic hydrocarbons such as kerosene gas oil or the like; aromatic hydrocarbones such as xylene, trimethylbenzene, tetramethylbenzene, methylnaphthalene or solvent naphtha; halogenated hydrocarbons such as chlorobenzene, acid amides such as dimethylacetamide; esters such as glycerine ester of a fatty acid; nitriles such as acetonitrile; or sulfur-containing compounds such as dimethyl sulfoxide; combinations of the foregoing; etc.

The active compounds described herein may be used alone or in combination with other active compounds such as insecticides, miticides, nematicides, fungicides, antiviral agents, attractants, herbicides or plant growth regulators, as desired. Such other compounds include, but are not limited to, those set forth in U.S. Pat. No. 5,360,806 at column 12, line 25 to column 18, line 8.

The active compounds described herein are applied as an active ingredient concentration of from 0.1 to 500,000 ppm, preferably from 1 to 100,000 ppm. The active ingredient concentration may optionally be changed depending upon the formulation, the manner, purpose, timing or place of the application, and the condition of the plants and risk of frost or freeze damage.

The amount of the application of the active ingredient per unit surface area is usually from about 0.1 to 5,000 g, preferably from 10 to 1,000 g, per hectare. However, in some cases, the amount of the application may be outside this range.

Various formulations containing the compounds of the present invention or their diluted compositions may be applied to plants by conventional methods for application, including but not limited to spraying (e.g., spraying, jetting, misting, atomizing, powder or grain scattering or dispersing in water), soil application (e.g., mixing or drenching), surface application (e.g., coating, powdering or covering), impregnation, etc. The applying step may be carried out by a so-called ultra low-volume application method, in which the composition or formulation applied consists essentially of the active agent.

Active agents may be applied as a salt with an acidic substance or a basic substance. The salt with an acidic substance may be an inorganic salt such as a hydrochloride, a hydrobromide, a phosphate, a sulfate, a nitrate, etc. The salt with a basic substance may be a salt of an inorganic or organic base, such as a sodium salt, a potassium salt, a calcium salt, an ammonium salt or a dimethylamine salt.

Fluazinam is, advantageously, rapidly and extensively degraded in the environment. The field soil dissipation half-life ranges from 6 to 49 days. The low seasonal use rate limits the amount of product in the environment. The aerobic aquatic half-life is 18 to 26 hours where extensive degradation leads to a large number of degradates. Due to fluazinam's low water solubility (0.071 ppm at pH 7) and high soil adsorption (Koc ranging from 1700 to 2300), it has very low potential to leach to ground water. While fluazinam can reach surface water via run-off or drift, the rapid and extensive degradation makes it extremely unlikely that fluazinam will persist in surface waters.

A preferred formulation of fluazinam for use in carrying out the present invention is OMEGA 500F™ agricultural fungicide, which comprises fluazinam (40.0%) and inert ingredients (60.0%), and contains 4.17 pounds fluazinam per gallon 500 grams per liter. OMEGA 500F™ agricultural fungicide is available from ISK Biosciences Corporation, 5970 Heisley Road, Ste. 200, Mentor, Ohio 44060 USA. In use, OMEGA 500F™ fungicide is applied with ground equipment in sufficient water to obtain adequate coverage of foliage. Gallons to be used will vary with crop and amount of plant growth. Spray volume usually will range from 20 to 60 gallons per acre (200 to 600 liters per hectare) for dilute sprays and 5 to 10 gallons per acre (50 to 100 liters per hectare) for concentrate ground sprays. An example spraying rate for OMEGA 500F™ formulation is as set forth in Table 1 below.

TABLE 1

APPLICATION RATE AND TIMING USING INTEGRATED PEST MANAGEMENT (IPM) TECHNIQUES

| CROP | RATE PER ACRE |
| --- | --- |
| Peanut | 1 pint |

APPLICATION DIRECTIONS

Apply with ground application equipment only, when vines are 6 inches from touching and weather conditions are favorable according to the Sclerotinia blight advisory.
Make a second application if weather conditions remain favorable, but not within 3 weeks of the first spray.
A third application can be made if disease conditions remain favorable but not within 3 weeks of the second application. DO NOT apply within 30 days of threshing for harvest.

Plants may be treated individually or as crops of like plants planted in an agricultural field of such plants, in which case the crop is treated as described above with respect to plants. Typically, the plants are harvested after they are treated, although the present invention may be carried out on plants that are not harvested (e.g. ornamental plants, particularly flowers). By "harvesting" is meant collection of the entire plant or a plant part such as a flower, leaf, stem, root, tuber, fruit, vegetable, etc. An advantage of the instant invention is the long duration of action of the active agent. Thus, the harvesting step may be carried out one week, one month, two months or more after the last application of the active agent, with the active agent still being effective to reduce frost damage during the intervening period.

The present invention is explained in greater detail in the following non-limiting Examples.

EXAMPLE 1

Peanut Field Studies

A peanut field was fumigated on April 28 with Metam sodium to control Cylindrocladium. The test plants were planted on May 22 with 16 different varieties of seed (Andru 93; Georgia Green; Tam Run 98; AT120; Southern Runner; Georgia Gold; Georgia Runner; 6K7WIDLEIL; FLA97R; FLAMDR98; FLA84x9B; NC7; VA93B; Perry; VA92R; VA98R), with a two-row planter. Temik and rhizobium were applied in furrow at standard rates. The spray date for the first treatment was July 20; the spray date for the second treatment was August 19. A tractor-mounted sprayer was used for all treatment sprays, with three hollow-cone nozzles per row at 40 psi, and 15 gal water/acre, at a height to cover the entire plant. Only the two treatment rows were sprayed. There were two unsprayed border rows between each treatment, to minimize interplot interference, and to assure even distribution of disease across plots. Herbicides, insecticides, and early leafspot control were applied according to standard practices across the field. Particular treatments were as follows:

(1) untreated control
(2) 15.22 fl. oz. Omega 500™ fluazinam 500F/acre (per spray)
(3) 30.44 fl. oz. Omega 500™ fluazinam 500F/acre (per spray)
(4) 60.88 fl. oz. Omega 500™ fluazinam 500F/acre (per spray)
(5) 32.0 fl. oz. Rovral™ brand iprodione+7.68 fl. oz. Nufilm™ adjuvant per acre (per spray)

(Rovral™ is the trade name for iprodione ($C_{13}H_{13}Cl_2N_3O_3$) CAS# 36734-19-7, a foliar fungicide which is the only currently registered fungicide available to control Sclerotinia blight. Nufilm™ is an adjuvant that is recommended for use with Rovral™).

Frost occurred on October 25. Frost ratings were done on November 2d. Rating Index: 1<5% green leaves, 4>50% green leaves; values between 1 and 4 were scaled from 5 to 50%. Stems were not rated, and varied from completely brown, to black, to bright green. When rating percentage of green leaves in a plot, those obviously dead from disease were ignored, and the rating was based on the remaining leaves.

Peanuts were dug on November 10, and harvested on November 15. Moisture samples were taken from untreated plots of each variety. Yields were adjusted to 9% moisture.

Data: Statistics were run using the SAS System using the General Linear Models Procedure. Results are as set forth in Tables 2–7 below.

TABLE 2

Dependent Variable: Frost Injury

| | Frost Mean Pr > F |
| --- | --- |
| Model | 0.0001 |
| Treatment | 0.0001 |
| Cultivar | 0.0001 |
| Treatment vs Cultivar | 0.1971 |

The data set forth in Table 2 indicates that there was a treatment effect (fluazinam), and a cultivar effect, but not an interaction effect in respect to frost.

TABLE 3

Dependent Variable: Disease Incidence

| | Disease Mean Pr > F |
| --- | --- |
| Treatment | 0.0001 |
| Cultivar | 0.0001 |
| Treatment vs Cultivar | 0.0586 |

The data set forth in Table 3 indicates that there was a treatment effect (fluazinam), and a cultivar effect, but not an interaction effect in respect to disease.

TABLE 4

Dependent Variable: Yield/Acre

| | Yield/Acre Mean Pr > F |
| --- | --- |
| Treatment | 0.0001 |
| Cultivar | 0.0001 |
| Treatment vs Cultivar | 0.0586 |

The data set forth in Table 4 indicates that there was a treatment effect (fluazinam), and a cultivar effect, but not an interaction effect in respect to yield per acre.

TABLE 5

Dependent Variable: Frost Injury

|  | Pr > \|T\| |
|---|---|
| High Rate vs Control | 0.0001 |
| High Rate vs Rovral | 0.0001 |

The data set forth in Table 5 indicates that the high rate of fluazinam treatment gave statistically significantly better frost protection as compared to both the Untreated Control and the Rovral treatments.

TABLE 6

Dependent Variable: Disease Incidence.

|  | Pr > \|T\| |
|---|---|
| High Rate vs Control | 0.0001 |
| High Rate vs Rovral | 0.3911 |

The data set forth in Table 6 indicates that the high rate of fluazinam treatment gave statistically significantly better disease control than the Untreated Control treatment, but not significantly better than the Rovral treatment.

TABLE 7

Dependent Variable: Yield/Acre.

|  | Pr > \|T\| |
|---|---|
| High Rate vs Control | 0.0001 |
| High Rate vs Rovral | 0.0001 |

The data set forth in Table 7 indicates that the high rate of fluazinam treatment resulted in yields that were statistically significantly higher than both the Untreated Control and the Rovral treatments.

Discussion: Fluazinam significantly reduced frost injury and Sclerotinia blight on various peanut cultivars. Peanut cultivars varied in their resistance to frost and disease injury. There was no interaction between fluazinam and cultivars regarding frost protection and disease.

Yields were significantly higher with fluazinam and some cultivars were higher yielding than others. There were no interactions between fluazinam and cultivars regarding yield.

Fluazinam at the highest tested rate protected plants from frost. The protection was unrelated to disease control. Yield increases from use of fluazinam probably resulted from less frost injury. Some yield increase could have resulted from undetected subterranean disease control effected by fluazinam above and beyond Rovral control, however, in the previous year's test in which no frost occurred there was no statistically significant difference in yield between the treatments, which would tend to discount this possibility.

A significant observation was that there was a 66-day lapse between the last treatment application and the frost event, and a 90-day lapse between the last treatment application and harvest. It is unlikely that significant active compound was still present as the half-life of the compound is approximately 24 hours in inundated soils. Record rains occurred in this field during this intervening period creating extended periods of extremely wet conditions. Therefore, it is likely that the frost protection was a systemic physiological response to the compound rather than a direct effect on the compound on ice crystal formation. Another possible explanation is that some leaf surface microorganisms are known to affect ice crystal formation and hence, plant vulnerability to frost injury. Fluazinam application could have modified the population to render it more protective than the native population. This explanation seems unlikely, as the intervening period should have allowed for the repopulation of the native leaf surface flora.

In summary, fluazinam has the potential to change peanut plants in such a way as to reduce frost injury and affect a corresponding yield increase.

The foregoing is illustrative of the present invention, and is not to be construed as limiting thereof. The invention is defined by the following claims, with equivalents of the claims to be included therein.

That which is claimed is:

1. A method of reducing cold injury to a plant, comprising applying a compound of formula I to said plant in an amount effective to reduce cold injury to said plant, wherein formula I comprises:

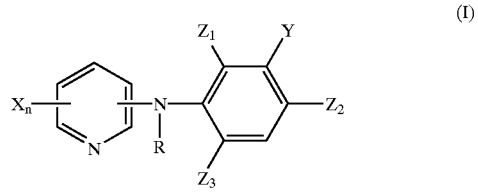

(I)

wherein X is a trifluoromethyl group, a halogen atom, a lower alkyl group or a lower alkoxy group; n is an integer of 0 to 4; R is a hydrogen atom or an acetyl group; Y is a hydrogen atom, a halogen atom, a lower alkoxy group, a lower alkylthio group, a hydroxy group, an azido group or a phenoxy group of which the phenyl ring may be substituted by a hydroxy group; and $Z_1$, $Z_2$, and $Z_3$ are independently a trifluoromethyl group or a nitro group; provided that at least one of X is a trifluoromethyl group or a lower alkyl group when n is an integer of 3 or 4.

2. A method according to claim 1, wherein said applying step is followed by the step of harvesting said plant.

3. A method according to claim 2, wherein said harvesting step is carried out at least one week after said applying step.

4. A method according to claim 2, wherein said harvesting step is carried out at least one month after said applying step.

5. A method according to claim 2, further comprising the step of subjecting said plant to frost between said applying step and said harvesting step.

6. A method according to claim 1, wherein said applying step is carried out by spraying.

7. A method according to claim 1, wherein said plant is a peanut plant.

8. A method according to claim 1, wherein said plant is a peach tree.

9. A method according to claim 1, wherein said plant is a strawberry plant.

10. A method according to claim 1, wherein said plant is a citrus tree.

11. A method of reducing frost injury to a plant, comprising applying a compound of formula I to said plant in an amount effective to reduce frost injury to said plant, wherein formula I comprises:

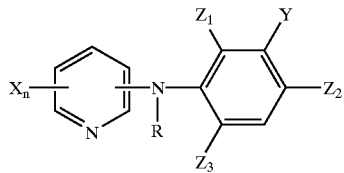

(I)

wherein X is a trifluoromethyl group, a halogen atom, a lower alkyl group or a lower alkoxy group; n is an integer of 0 to 4; R is a hydrogen atom or an acetyl group; Y is a hydrogen atom, a halogen atom, a lower alkoxy group, a lower alkylthio group, a hydroxy group, an azido group or a phenoxy group of which the phenyl ring may be substituted by a hydroxy group; and $Z_1$, $Z_2$, and $Z_3$ are independently a trifluoromethyl group or a nitro group; provided that at least one of X is a trifluoromethyl group or a lower alkyl group when n is an integer of 3 or 4.

12. A method according to claim 11, wherein said applying step is followed by the step of harvesting said plant.

13. A method according to claim 12, wherein said harvesting step is carried out at least one week after said applying step.

14. A method according to claim 12, wherein said harvesting step is carried out at least one month after said applying step.

15. A method according to claim 12, further comprising the step of subjecting said plant to frost between said applying step and said harvesting step.

16. A method according to claim 11, wherein said applying step is carried out by spraying.

17. A method according to claim 11, wherein said plant is a peanut plant.

18. A method according to claim 11, wherein said plant is a peach tree.

19. A method according to claim 11, wherein said plant is a strawberry plant.

20. A method according to claim 11, wherein said plant is a citrus tree.

* * * * *

UNITED STATES PATENT AND TRADEMARK OFFICE
CERTIFICATE OF CORRECTION

PATENT NO. : 6,588,142 B2
DATED : July 8, 2003
INVENTOR(S) : Curtis et al.

It is certified that error appears in the above-identified patent and that said Letters Patent is hereby corrected as shown below:

<u>Title page</u>,
Item [56], References Cited, OTHER PUBLICATIONS, the fifth reference should read -- Ritchie, D.F. and W. Pollard, 1996, Fluazinam 500F for Control of Bacterial Spot of Peach, 1995, Fungicide and Nematicide Tests 51:54 --

Signed and Sealed this

Twenty-first Day of September, 2004

JON W. DUDAS
*Director of the United States Patent and Trademark Office*